Figures 1, 2, 3:
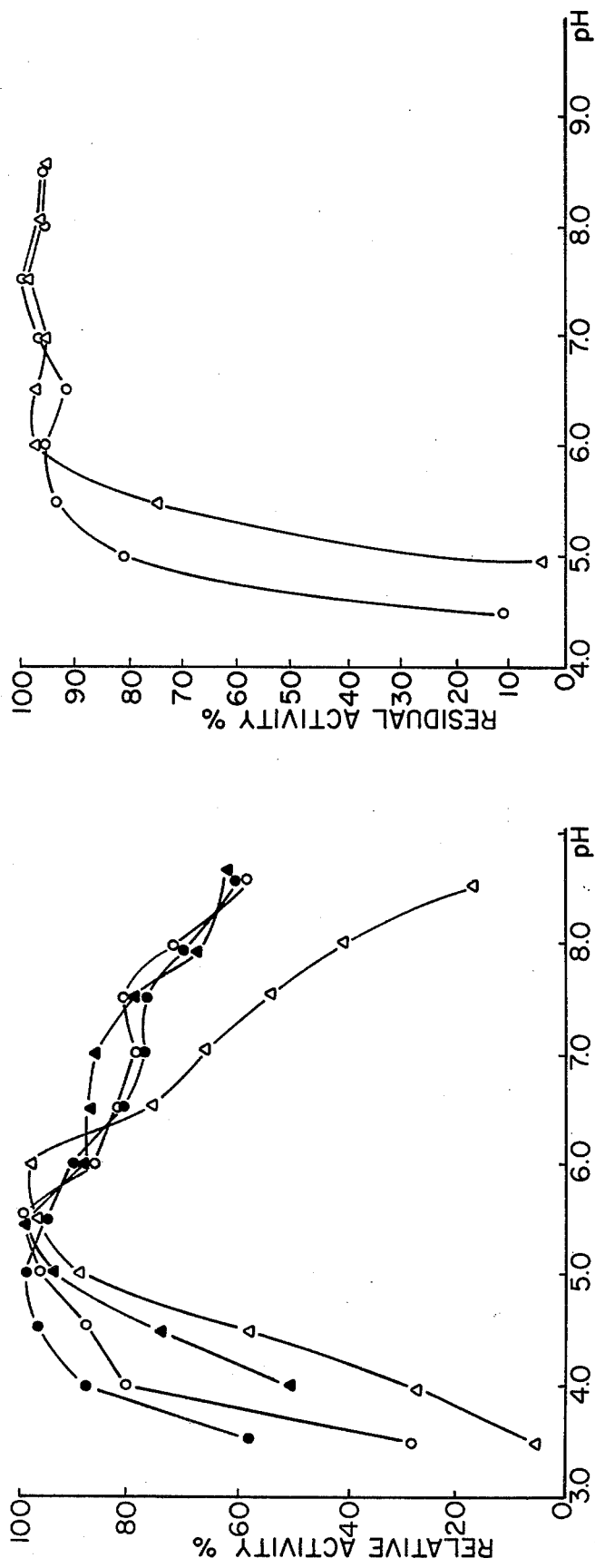

United States Patent [19]
Shiosaka

[11] 3,988,206
[45] Oct. 26, 1976

[54] HEAT STABLE CYCLODEXTRIN GLYCOSYLTRANSFERASE

[75] Inventor: Makoto Shiosaka, Okayama, Japan

[73] Assignee: Hayashibara Biochemical Laboratories, Incorporated, Japan

[22] Filed: Sept. 23, 1974

[21] Appl. No.: 508,433

[30] Foreign Application Priority Data
Oct. 2, 1973    Japan............................ 48-110868

[52] U.S. Cl.............................. 195/62; 195/31 R; 195/63; 195/66 R
[51] Int. Cl.².......................................... C07G 7/02
[58] Field of Search............ 195/62, 65, 66 R, 31 R

[56] References Cited
UNITED STATES PATENTS
3,697,378   10/1972   Smalley............................ 195/31 R
3,812,011   5/1974   Okada et al...................... 195/31 R OTHER PUBLICATIONS
Chemical Abstracts, vol. 73, 41969y, (1970).
Chemical Abstracts, vol. 79, 122944n, (1973).

Primary Examiner—David M. Naff
Attorney, Agent, or Firm—Hans Berman

[57] ABSTRACT

A cyclodextrin glycosyltransferase having high heat stability is obtained from the cell-free broth of a culture of Bacillus stearothermophilus. The cyclodextrin glycosyltransferase gives higher yields of cyclodextrin from starch and higher transfer ratios of glucose in starch or partial starch hydrolyzate to sucrose than known cyclodextrin glycosyltransferases.

4 Claims, 6 Drawing Figures

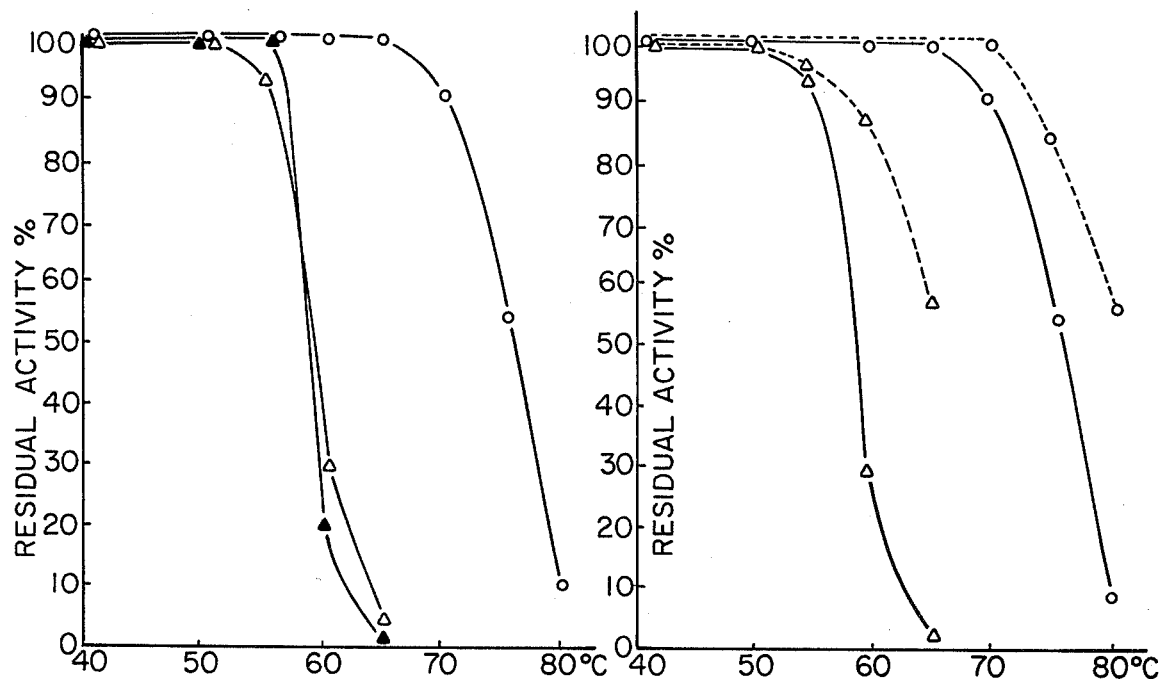
FIG.4
FIG.5
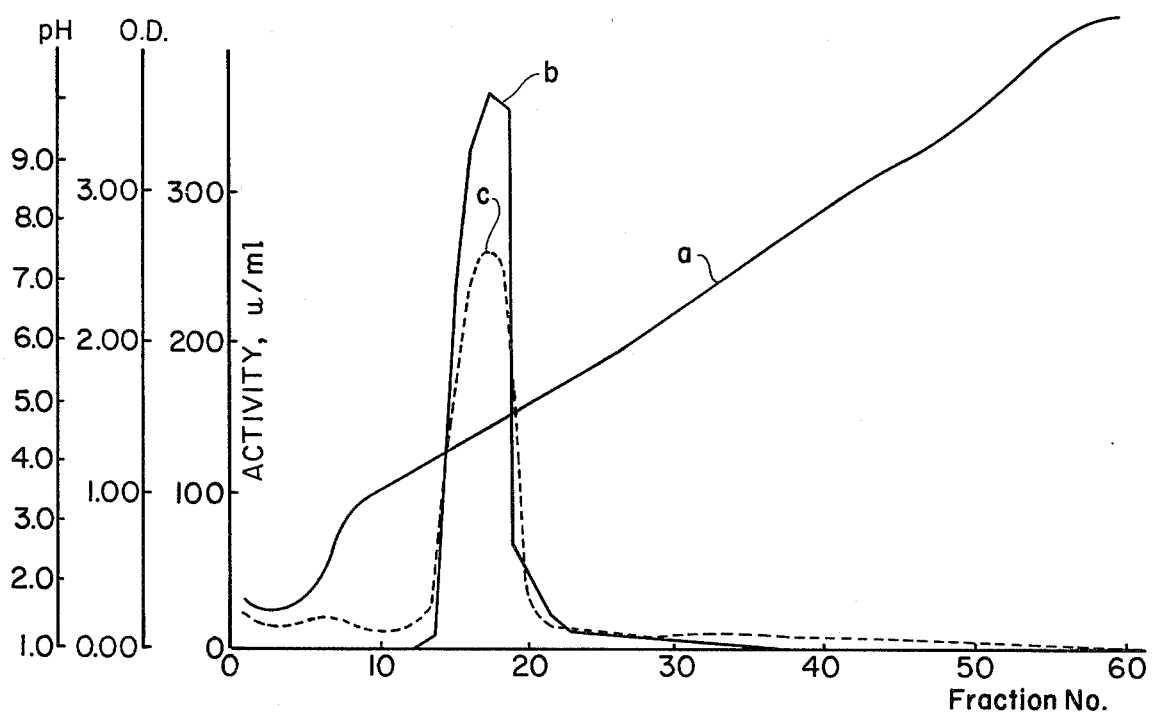
FIG.6

HEAT STABLE CYCLODEXTRIN GLYCOSYLTRANSFERASE

This invention relates to cyclodextrin glycosyltransferase and particularly to the preparation thereof by microorganisms.

It is known that cyclodextrin glycosyltransferase (E.C. 2.4.1.19, hereinafter abbreviated as CGT) produced by *Bacillus macerans* is capable of acting on starch solutions and forming cyclodextrin consisting of six or more alpha-D-glucose residues, and it is also capable of acting on a solution of starch and sucrose and transferring glucose contained in starch or partial starch hydrolyzate to the glucose moiety in the sucrose molecule.

Recently certain strains of *Bacillus megaterium* were also reported to produce CGT (Sumio Kitahata, Naoto Tsuyama and Shigetaka Okada: Proceedings of the Symposium on Amylase, Vol 7, 61–68 (1972)).

The present inventor isolated strains of *Bacillus stearothermophilus* from soil and discovered that they produce CGT.

The CGT produced by *Bacillus stearothermophilus* has better heat stability, gives higher yields of cyclodextrin from starch, and gives higher transfer ratios of glucose in starch or partial starch hydrolyzate to sucrose as compared to known CGT.

*Bacillus macerans* CGT was reported by E. B. Tilden and C. S. Hudson in "The Journal of the American Chemical Society," Vol. 61, 2900–2902, 1939). This CGT acts on starch solution to form at first α-cyclodextrin consisting of six glucose residues and next β-cyclodextrin consisting of seven glucose residues. If the solution contains a glucose acceptor such as sucrose, the CGT transfers glucose from starch to the acceptor.

The enzymes of *Bacillus stearothermophilus* and *Bacillus macerans* differ in heat stability. When both enzymes were allowed to stand at various temperatures for 15 minutes, the residual activity of *Bacillus macerans* CGT was 100% at 50° C and 30% at 60° C, whereas that of *Bacillus stearothermophilus* CGT remained 100% even at a temperature of 65° C. Since a 15° C increase in temperature increases the reaction rate and protects the reaction mixture from contamination by microorganisms, *Bacillus stearothermophilus* CGT is more advantageous in industrial practice.

When the ability of transferring glucose to sucrose (hereinafter referred to as transfer activity) is expressed as the ratio of hydrolysis activity (dextrinogenic activity) in a sucrose-bearing starch solution to that in a solution containing starch only, the transfer activity of *Bacillus macerans* CGT is 0.58, while that of *Bacillus stearothermophilus* CGT is about 1.62 – 1.84.

The effects of *Bacillus megaterium* and *Bacillus stearothermophilus* CGTs on solutions containing sucrose and starch were compared, and the observed enzyme activities were expressed in dextrinogenic activities necessary to give a 50% or higher ratio of glucose-transferred sucrose to the total sucrose employed. The test showed that *Bacillus stearothermophilus* CGT permits the same transfer ratio to be attained at 1/7 of the dextrinogenic activity required for *Bacillus megaterium* CGT.

When *Bacillus macerans* CGT was added to a starch solution in an amount of 10 units of dextrinogenic activity per gram starch and the solution was allowed to stand at 55° C, cyclodextrin was obtained in a 43% yield from starch, whereas *Bacillus stearothermophilus* CGT gave a 56% yield when the amount employed was 1/10 of that of *Bacillus macerans* CGT.

Nine strains of *Bacillus stearothermophilus* FERM-P Nos. 2217, 2218, 2219, 2220, 2221, 2222, 2223, 2224 and 2225 were isolated from soil. Cultivation tests were carried out on a medium containing, in grams per deciliter,

| | |
|---|---|
| Soluble starch | 2 |
| $NH_4Cl$ | 0.5 |
| $K_2HPO_4$ | 0.05 |
| $MgSO_4 \cdot 7H_2O$ | 0.025 |
| $CaCO_3$ | 0.5 |

50 Ml portions of the medium were poured into 500 ml Erlenmeyer flasks, inoculated and cultured at a temperature of 50° to 55° C for 50 hours on a rotary shaker. The optimum temperature for cultivation was determined in temperature gradient incubator Model TN-3 (Toyo Kagaku Sangyo Ltd., Tokyo Japan) from 20° to 80° C. The test showed that turbidity and activity of the culture broths were high from 40° to 55° C, and highest at 50° C.

The seed culture was prepared by shaking at 50° C for 15 hours and inoculated on the main culture medium after undergoing heat shock. The heat shock was effective at 60° to 100° C for less than 30 minutes. Especially when the seed culture was treated at 98° C for 6 minutes or at 80° C for 30 minutes, the activity of the main culture broth at least doubled.

To obtain the maximum enzyme activity during the cultivation, aeration to an oxygen absorption ratio of not less than 0.2 mmol $O_2$/l/min was required.

At least 48 hours cultivation time was required for maximum enzyme yield.

A. Taxonomic description of isolated microorganisms a. Morphological characteristics
  Forms: Rods, 0.5 to 1.0 by 3.0 to 10.0 microns, occurring in filaments or in chains. Motile.
  Spores: 1.0 to 1.2 by 1.5 to 2.2 microns, ellipsoidal in racket-shaped sporangia.
  Agar colonies: Large, smooth, spreading, whitish, translucent.
  Bouillon agar slants: Growth
  Glucose bouillon agar slants: Growth less than on bouillon agar slants.
  Potato: Scant, if any, growth.
  Soybean agar slants: Growth less than on bouillon agar slants.

b. Physiological characteristics
  Growth optimum: 50° and 65° C, pH 7.0, aerobic.
  Gram stain: Gram-variable.
  Catalase: Positive
  Utilization of citrate as sole source of carbon: Not utilized.
  Acetylmethylcarbinol: Not produced.
  Nitrate reduction: Nitrite not produced from nitrate.
  Hydrolysis of starch: Hydrolyzed.
  Gelatin stab: Liquefaction.
  Milk agar streak plate: Hydrolysis or no hydrolysis of casein.

c. Utilization of sugars
  Acid but no gas from glucose.
  Acid or no acid from arabinose.
  Acid or no acid from mannitol.

No acid from lactose.

B. Identification of the microorganisms of the present invention

The microorganisms isolated were classified by the method reported by Smith, Gordon and Clark et al. in "Agricultural Monograph 16," U.S. Department of Agriculture, 1952.

The nine microorganisms are similar to *Bacillus macerans* in being capable of producing cyclodextrin-forming enzymes. They are, however, different from *Bacillus subtilis*, *Bacillus licheniformis* and *Bacillus coagulans* in being incapable of forming acetylmethylcarbinol and are also different from these three microorganisms and from *Bacillus megaterium* in not utilizing citrate. Accordingly, the microorganisms of the present invention may belong to *Bacillus stearothermophilus*, *Bacillus macerans* or *Bacillus circulans*.

The microorganisms of the present invention were compared with *Bacillus stearothermophilus* ATCC 21356, *Bacillus macerans* IFO 3490 and *Bacillus circulans* ATCC 4513 and agreed with *Bacillus stearothermophilus* in their optimal growth temperature in 50° to 60° C and of not growing at 28° C.

The newly isolated microorganisms are apparently different from *Bacillus macerans* or *Bacillus circulans* in not growing on a medium containing 3% NaCl, in not producing gas, in forming acids from glucose and in hydrolyzing casein.

Based on the above mentioned observations, the isolated microorganisms of the present invention were identified as *Bacillus stearothermophilus*.

The strains FERM-P Nos. 2217, 2219 and 2224 formed acids from arabinose, while no formation of such acids was noted with the other six strains FERM-P Nos. 2218, 2220, 2221, 2222, 2223 and 2225. In addition, FERM-P Nos. 2222 and 2224 did not form acids from mannitol, while the others did.

Among the nine strains, only FERM-P No. 2217 did not hydrolyze casein. Also the growth temperature of each stain was found to be slightly different. FERM-P No. 2219 grew at 60° C, but not at 65° C, while the other eight grew at 65° C.

FERM-P Nos. 2220, 2221 and 2223 grew better on the soybean-agar slant than on the nutrient agar slant, while the others showed the opposite behavior.

There was hardly any difference in enzyme properties among the CGTs produced by the nine strains, and experimental data on purification and properties for the CGTs of representative strains will be illustrated. Enzymatic activities were determined measuring dextrinogenic activity and cyclodextrin-producing activity by the Tilden-Hudson method (E. B. Tilden and C. S. Hudson; J. Bact., 43, 727–744, 1942), and the transfer ratio of glucose to sucrose. As correlation was noted between the activities and the absence of α-amylase, the determination methods were found to be quantitatively accurate. Based on these findings, enzymatic activity was determined mainly by dextrinogenic activity measurement.

Transfer activity to sucrose

One ml of an enzyme solution was added to 3 ml of a solution containing 6.7 g/dl soluble starch, 6.7 g/dl sucrose, $2 \times 10^{-3}$ M $CaCl_2$ and 0.03 M acetate buffer, pH 5.5. After incubation for 10 minutes at 40° C, 0.5 ml of the mixture was poured into 9 ml of 1 N HCl to terminate the reaction. A 0.05 ml sample was poured into 15 ml of 0.02 N $H_2SO_4$, and after admixing thereto 0.2 ml of a 0.1 N $I_2$-KI solution, the optical density of the mixture was determined at 660 nm. One unit of activity was designated as the amount of enzyme that caused a 10% reduction in iodine stain of 200 mg soluble starch at 40° C within 10 minutes.

Dextrinogenic activity

A mixture prepared by adding 0.2 ml of an enzyme solution to 5 ml of a solution containing 0.3 g/dl soluble starch, 0.02 M acetate buffer, pH 5.5 and $10^{-3}$ M $CaCl_2$ was allowed to react at 40° C for 10 minutes. 0.5 ml Reaction mixture was collected, poured into 15 ml of 0.02 N $H_2SO_4$ to terminate the reaction and assayed for optical density at 660 nm after addition of 0.2 ml of 0.1 N $I_2$-KI solution. One unit of activity was designated as the amount of enzyme that caused disappearance of iodine stain in 15 mg soluble starch at 40° C within 10 minutes.

Enzyme purification

A culture broth of *Bacillus stearothermophilus* FERM-P No. 2218 was centrifuged to remove cells and $(NH_4)_2SO_4$ was added to the supernatant to 15% saturation. The solution was passed through a starch column. The adsorbed enzyme was eluted from the starch with water, $(NH_4)_2SO_4$ was added to the eluate, and the precipitates formed between saturations of 25 and 50% were recovered and subjected to gel fractionation to purify the enzyme. The results are shown in Table 1.

Table 1

| Step | Activity (U/ml) | Volume (ml) | Total activity(U) | Specific activity (U/mg protein) | Yield (%) |
|---|---|---|---|---|---|
| Supernatant culture broth | 10.4 | 1180 | $1.23 \times 10^4$ | 1.27 | 100 |
| Eluate from starch | 40.4 | 300 | $1.21 \times 10^4$ | 5.6 | 99 |
| $(NH_4)_2SO_4$ precipitate | 1020 | 10.7 | $1.09 \times 10^4$ | 52.3 | 89 |
| Gel fractionation by biogel 150 | 128 | 80 | $1.02 \times 10^4$ | 129 | 82.3 |

Assay of the purified CGT by disc gel electrophoresis and isoelectric focusing showed a single absorbance peak. The isoelectric point of the CGT was at pH 4.45.

In the attached drawing,

FIGS. 1 to 5 graphically illustrate the results of comparison tests of CGT of this invention as compared to known CGT, and FIG. 6 similarly illustrates tests of the CGT of this invention.

Properties of the CGTs

The CGTs produced by *Bacillus stearothermophilus* FERM-P Nos. 2218 and 2222, *Bacillus megaterium* FERM-P No. 935 and *Bacillus macerans* IFO 3490 are identified in FIGS. 1 to 5 by the followng symbols:

white circle *Bacillus stearothermophilus* FERM-P No. 2218
black circle *Bacillus stearothermophilus* FERM-P No. 2222
black triangle *Bacillus megaterium* FERM-P No. 935
white triangle *Bacillus macerans* IFO 3490

1. Optimal pH

The purified CGTs were assayed for their dextrinogenic activity with an acetate buffer at pH 3.5 to 6.0 and with a Tris-maleic acid buffer at pH 6.5 to 8.5, for optimum pH.

FIG. 1 illustrates the variation of dextrinogenic activity of CGT produced by the afore-mentioned four strains with pH, the activity being plotted in percent of the maximum activity observed for each strain. *Bacillus stearothermophilus* FERM-P No 2218 and 2222 CGTs showed a strong activity in a wider pH range, and the CGTs produced by *Bacillus megaterium* FERM-P No. 935 and *Bacillus macerans* IFO 3490.

The activity of *Bacillus stearothermophilus* CGT was highest at pH 5.0 to 5.5, which was slightly lower than the optimum pH for the other two CGTs.

2. Optimal temperature

The results shown in FIG. 2 were obtained by determining variation of dextrinogenic activity and Tilden-Hudson activity of the CGTs as a function of temperature.

When the activity at 40° C was expressed as 100%, the activities of *Bacillus stearothermophilus* FERM-P Nos. 2218 and 2222 CGTs were 450 to 750% at 70° to 80° C. The temperature range of 70° to 75° C is optimum for the CGTs.

The CGTs produced by *Bacillus macerans* IFO 3490 and *Bacillus megaterium* FERM-P No. 935 had an optimal temperature of 55° to 60° C, but their activities were only 250 to 300%.

3. pH stability

Enzyme solutions were adjusted with buffer solutions to different values and held at 40° C for 2 hours and the residual dextrinogenic activities of the solutions were then measured. FIG. 3 shows the residual activity in percent for each tested pH.

*Bacillus stearothermophilus* FERM-P No. 2218 CGT was found stable over a pH range of 5.0 to 8.0, a range wider than that of *Bacillus macerans* IFO 3490 CGT.

4. Heat stability

After the purified CGTs were allowed to stand at various temperatures for 15 minutes in M/50 Tris-HCl buffer solution of pH 7.0, their dextrinogenic activity was determined. FIG. 4 shows residual activity in percent. The CGTs of *Bacillus megaterium* FERM-P No. 935 and *Bacillus macerans* IFO 3490 suddenly lost their activities at a temperature of 55° C, while the CGT of *Bacillus stearothermophilus* did not lose its activity even at 65° C.

5. The effects of calcium chloride addition on heat stability

In FIG. 5, the solid lines were arrived at as in FIG. 4, while the broken lines show the effects of addition of $10^{-2}$ M calcium chloride.

The addition of calcium chloride in $10^{-4}$ to $10^{-2}$ M to the CGTs produced by *Bacillus stearothermophilus* FERM-P No. 2218 and *Bacillus macerans* IFO 3490 caused a 5° C rise in the limit of heat stability. The initial 15° C difference in the limits of heat stability between the enzymes remained unchanged.

6. Molecular weight

The ultracentrifugal pattern of the purified CGT produced by *Bacillus stearothermophilus* FERM-P No. 2218 showed a single symmetric peak. The sedimentation constant, $S_{20}w$, calculated from the sedimentation coefficients at enzyme protein concentrations of 1.3 g/dl, 1.0 g/dl and 0.65 g/dl was $(5.755 \text{ to } 5.81) \times 10^{-13}$ and the diffusion constant measured with synthetic boundary cells was $\Delta D > av = 7.23 \times 10^{-7}$. Thus, the molecular weight can be calculated from the formula: $RST/(1-Vp) D$, wherein
$R$ is the gas constant;
$T$ is the absolute temperature;
$S$ is the sedimentation constant;
$D$ is the diffusion constant;
$V$ is the partial specific volume; and
$P$ is the solvent density.

By substituting 0.735 for $V$ in the above formula, the molecular weight of the enzyme was determined as $70,000 \pm 40,000$.

7. Determination of isoelectric point

Isoelectric-focusing tests were carried out at 4° C using a column with a capacity of 110 ml, LKB Model 8100 Ampholine Electrofocusing Equipment (a product of L.K.B., Sweden). The carrier ampholyte, covering a pH range between 3 and 10, was used at an average final concentration of 1%. 60 Sequential fractions were each tested for pH, dextrinogenic activity in units per milliliter, and optical density at 280 nm.

The results are shown in FIG. 6, wherein the curve *a* shows pH; *b* dextrinogenic activity; and *c* variation of O.D. 280.

Since the purified CGT produced by *Bacillus stearothermophilus* FERM-P No. 2218 showed a single peak, its isoelectric point was determined as pH 4.45.

CGT acting on solutions containing sucrose and either starch or partial starch hydrolyzate causes the transfer of glucose from the starch of partial starch hydrolyzate to the sucrose to form oligoglucosylfructose. A non-crystallizing syrup of unique sweetness is obtained.

*Bacillus stearothermophilus* CGT of the present invention was compared with the previously known CGTs produced by *Bacillus macerans* and *Bacillus megaterium* for transfer activity. Table 2 gives the results.

Table 2

| Relative activity per unit of dextrinogenic activity | | | |
|---|---|---|---|
| | Dextrinogenic activity | Tilden-Hudson activity | Transfer activity to sucrose |
| *Bacillus macerans* IFO 3490 | 1.00 | 6.07 | 0.58 |
| *Bacillus megaterium* FERM-P No. 935 | 1.00 | 0.00 | 1.00 |
| *Bacillus stearo-thermophilus* FERM-P No. 2218 | 1.00 | 2.78 | 1.62 |
| *Bacillus stearo-thermophilus* FERM-P No. 2222 | 1.00 | 4.85 | 1.84 |

*Bacillus megaterium* FERM-P No. 935 CGT did not show any Tilden-Hudson activity. However, *Bacillus stearothermophilus* CGT of the present invention resembles *Bacillus macerans* IFO 3490 CGT as both enzymes show Tilden-Hudson activity.

The CGTs produced by *Bacillus stearothermophilus* FERM-P Nos. 2218 and 2222 are quite different from the CGTs produced by *Bacillus macerans* and *Bacillus megaterium* in that the transfer activity of the new enzymes is about 2 to 3 times higher than the transfer activity of the known enzymes.

The differences in transfer ratio and cyclodextrin yield between *Bacillus stearothermophilus* FERM-P No. 2218 CGT and *Bacillus megaterium* FERM-P No. 935 CGT were examined. Tables 3 and 4 show the results.

Comparison of the ratio of glucose-transferred sucrose

Enzyme solution was added to a solution of pH 6 containing 20% soluble starch, 20% sucrose and $2 \times 10^{-3}$ M $CaCl_2$, and the mixture was allowed to react at 65° C for 48 hours. The activities of the CGTs in Table 3 are given in terms of dextrinogenic activity.

Table 3

| Relation between enzyme activity and transfer ratio | | |
|---|---|---|
| | Activity (U/g starch) | Transfer ratio* (%) |
| *Bacillus stearothermophilus* FERM-P No. 2218 CGT | 1.4 | 50.3 |
| | 10.8 | 55.8 |
| *Bacillus megaterium* FERM-P No. 935 CGT | 10.0 | 50.3 |

*Transfer ratio is given in terms of ratio of glucose-transferred sucrose versus total sucrose employed, by determining ketoses paperchromatographically.

Relation between enzyme activity and cyclodextrin yield

8 Ml of water was added to 1 g starch, and the mixture was heated to gelatinize the starch and adjusted to pH 6.0 with a 0.5 M acetate buffer solution. An enzyme solution and 1 ml of toluene were added. After 3 days, the cyclodextrin which precipitated as toluene complex was determined.

Table 4

| | Cyclodextrin yield, % | | |
|---|---|---|---|
| | Activity (U/g starch) | Yield (%) 55° C | 65° C |
| *Bacillus stearothermophilus* FERM-P No. 2218 CGT | 1 | 56 | 56 |
| | 2 | — | 62 |
| | 5 | 49 | 63 |
| | 10 | 35 | 25 |
| *Bacillus macerans* IFO 3490 CGT | 1 | 4 | 4 |
| | 2 | — | 7 |
| | 5 | 48 | 15 |
| | 10 | 55 | 56 |

The activities of the CGTs in Table 4 are given in terms of dextrinogenic activity. The employment of one unit of *Bacillus stearothermophilus* FERM-P No. 2218 CGT per gram starch gave a 56% yield of cyclodextrin based on starch. The yield corresponded to that obtained by the employment of 10 units of *Bacillus macerans* IFO 3490 CGT. Two units of *Bacillus stearothermophilus* CGT gave a 62% cyclodextrin yield, a level which could not be reached by the employment of *Bacillus macerans* CGT. An excess employment of the enzyme resulted in a yield decrease.

As is evident from the foregoing results, *Bacillus stearothermophilus*, CGT not only has a wide heat stability range but also greatly reduces the enzyme activity required for the production of cyclodextrin and glucose-transferred sucrose while increasing yields, as compared to the CGTs produced by *Bacillus megaterium* and *Bacillus macerans*.

During cyclodextrin formation, unlike *Bacillus megaterium* CGT, the CGT of the present invention, at first, forms α-cyclodextrin and then β-cyclodextrin. The following examples will further illustrate this invention.

EXAMPLE 1

*Bacillus stearothermophilus* FERM-P Nos. 2217, 2218, 2219, 2220, 2221, 2222, 2223, 2224 and 2225, were cultured on a medium containing, in g/dl, %

| Soluble starch | 2 |
|---|---|
| $NH_4Cl$ | 0.5 |
| $K_2HPO_4$ | 0.05 |
| $MgSO_4$ | 0.025 |
| $CaCO_3$ | 0.5 |

50 Ml portions of the medium were transferred to 500 ml Erlenmeyer flasks, sterilized at 120° C for 30 minutes and inoculated with respective strains. The resulting mixtures were subjected to shaking culture at 50° C on a rotary shaker for 50 hours. The resultant culture broths were analyzed for their dextrinogenic activity, Tilden-Hudson activity and transfer activity to sucrose. Table 5 shows the results.

Table 5

| | *Bacillus stearothermophilus* FERM-P Nos. | | | | | | | | |
|---|---|---|---|---|---|---|---|---|---|
| | 2217 | 2218 | 2219 | 2220 | 2221 | 2222 | 2223 | 2224 | 2225 |
| Dextrinogenic activity (U/ml) | 0.5 | 2.7 | 0.4 | 0.9 | 0.9 | 6.8 | 3.5 | 3.0 | 17.0 |
| Tilden-Hudson activity (U/ml) | 1.5 | 6.0 | 1.0 | 3.0 | 2.0 | 20.0 | 8.0 | 10.0 | 80.0 |
| Transfer activity to sucrose (U/ml) | 0.8 | 4.2 | 0.6 | 1.6 | 1.1 | 9.0 | 5.0 | 5.0 | 34.0 |

EXAMPLE 2

10 Ml portions of the medium used in Example 1 were transferred to test tubes, sterilized, inoculated with the above-described nine strains respectively, subjected to shaking culture at 50° C for 15 hours and then heat-shocked by immersing the test tubes in water of 98° C for 6 minutes. 0.5 Ml portions of the broths were transferred to 50 ml portions of the same medium and cultivated at 50° C for 50 hours on a rotary shaker. The activities were determined in terms of dextrinogenic activity. The dextrinogenic results are shown in Table 6.

Table 6

| | Cultivation time | Bacillus stearothermophilus FERM-P Nos. | | | | | | | | |
|---|---|---|---|---|---|---|---|---|---|---|
| | | 2217 | 2218 | 2219 | 2220 | 2221 | 2222 | 2223 | 2224 | 2225 |
| Activity (U/ml) | 2 days | 1.0 | 4.0 | 0.5 | 0.9 | 1.9 | 6.2 | 8.4 | 6.5 | 14.3 |
| | 3 days | 1.2 | 5.1 | 0.6 | 0.9 | 1.8 | 7.9 | 8.4 | 6.6 | 14.7 |
| Turbidity* | 2 days | 0.402 | 0.805 | 0.315 | 0.381 | 0.410 | 0.445 | 0.600 | 0.445 | 0.720 |
| | 3 days | 0.391 | 0.743 | 0.305 | 0.400 | 0.400 | 0.305 | 0.610 | 0.420 | 0.670 |

*The culture broths were diluted ten times with 1/10 N HCl and then measured for optical density at 660 nm using a spectrophotometer (Hitachi Model 101) having a 1 cm cell.

The culture collections from which specimen cultures of microorganisms referred to herein are available are identified in this specification as follows:

IFO: Institute for Fermentation — Osaka City

FERM-P: Fermentation Research Institute, Agency of Industrial Science and Technology — Chiba City

What is claimed is:

1. A cyclodextrin glycosyltransferase capable of converting starch to cyclodextrin and of transferring glucose from starch to sucrose, said cyclodextrin glycosyltransferase maintaining substantially 100% activity for 15 minutes at 65° C in an aqueous M/50 solution of Tris-HCl buffer at pH 7.0 in the absence of calcium chloride.

2. A cyclodextrin glycosyltransferase as set forth in claim 1 which is an extracellular product of the microorganism Bacillus stearothermophilus.

3. A cyclodextrin glycosyltransferase as set forth in claim 1, said glycosyltransferase maintaining substantially 100% activity for 15 minutes at 70° C in an aqueous M/50 solution of Tris-HCl buffer at pH 7.0 in the presence of $10^{-2}$ mole calcium chloride.

4. A cyclodextrin glycosyltransferase as set forth in claim 2, whrein said microorganism is Bacillus stearothermophilus FERM-P 2217, 2218, 2219, 2220, 2221, 2222, 2223, 2224 and 2225.

* * * * *

UNITED STATES PATENT AND TRADEMARK OFFICE
CERTIFICATE OF CORRECTION

PATENT NO. : 3,988,206
DATED : October 26, 1976
INVENTOR(S) : Makoto Shiosaka

It is certified that error appears in the above—identified patent and that said Letters Patent are hereby corrected as shown below:

In the heading, line [73], after "Incorporated," insert --

Okayama-ken --.

Signed and Sealed this

Eleventh Day of January 1977

[SEAL]

Attest:

RUTH C. MASON
*Attesting Officer*

C. MARSHALL DANN
*Commissioner of Patents and Trademarks*